(12) United States Patent
Belongia

(10) Patent No.: US 10,363,333 B2
(45) Date of Patent: Jul. 30, 2019

(54) WAX WARMER

(71) Applicant: S.C. Johnson & Son, Inc., Racine, WI (US)

(72) Inventor: David C. Belongia, Burlington, WI (US)

(73) Assignee: S.C. JOHNSON & SON, INC., Racine, WI (US)

( * ) Notice: Subject to any disclaimer, the term of this patent is extended or adjusted under 35 U.S.C. 154(b) by 492 days.

(21) Appl. No.: 14/243,704

(22) Filed: Apr. 2, 2014

(65) Prior Publication Data

US 2015/0283280 A1    Oct. 8, 2015

(51) Int. Cl.
*A01G 13/06* (2006.01)
*A61L 9/03* (2006.01)

(52) U.S. Cl.
CPC ........... *A61L 9/03* (2013.01); *A61L 2209/133* (2013.01)

(58) Field of Classification Search
None
See application file for complete search history.

(56) References Cited

U.S. PATENT DOCUMENTS

| | | |
|---|---|---|
| 1,547,160 A | 5/1923 | Bailey |
| 2,465,762 A | 7/1945 | Supplee |
| 2,668,993 A | 8/1950 | Bair |
| 2,685,020 A * | 7/1954 | Laibow ............... A01M 1/2077 392/390 |
| 3,218,606 A * | 11/1965 | Schultz ................ H01R 12/718 439/82 |
| 3,255,430 A * | 6/1966 | Phillips ................ H01R 13/33 29/517 |
| 3,890,085 A | 6/1975 | Andeweg |
| 4,214,146 A | 7/1980 | Schimanski |
| 4,287,408 A | 9/1981 | Wilson |
| 4,696,303 A | 9/1987 | Bernardini |
| 4,731,522 A * | 3/1988 | Manchester ........ A01M 1/2077 219/433 |
| 4,781,895 A | 11/1988 | Spector |
| 5,578,089 A | 11/1996 | Elsamaloty |
| 5,945,094 A | 8/1999 | Martin et al. |
| 5,959,129 A | 9/1999 | van Dam et al. |
| 6,019,804 A | 2/2000 | Requejo et al. |
| 6,063,144 A | 5/2000 | Calzada et al. |
| 6,106,597 A | 8/2000 | Starks et al. |

(Continued)

FOREIGN PATENT DOCUMENTS

| | | |
|---|---|---|
| CN | 201779493 U | 3/2011 |
| WO | WO 2007/075645 A1 | 7/2007 |
| WO | 2010088175 A1 | 8/2010 |

OTHER PUBLICATIONS

PCT/US2015/023764 International Search Report and Written Opinion dated Jan. 16, 2015.

(Continued)

*Primary Examiner* — Thor S Campbell
(74) *Attorney, Agent, or Firm* — Quarles & Brady LLP

(57) ABSTRACT

A wax warmer includes a reservoir module for receiving a wax melt, a heater module, and a base module. The heater module includes a heating element. The reservoir module, the heater module, and the base module are removable from one another in the normal use of the wax warmer and may be replaced by a second reservoir module, a second heater module, or a second base module, respectively.

21 Claims, 15 Drawing Sheets

(56) References Cited

U.S. PATENT DOCUMENTS

| | | | |
|---|---|---|---|
| 6,214,918 B1 | 4/2001 | Johnson et al. | |
| 6,224,641 B1 | 5/2001 | Matzat et al. | |
| 6,284,007 B1 | 9/2001 | Tao | |
| 6,380,462 B1 | 4/2002 | Krindl | |
| 6,412,670 B1 * | 7/2002 | Randmae | C11C 5/023 222/452 |
| 6,413,476 B1 | 7/2002 | Barnhart | |
| 6,497,735 B2 | 12/2002 | Tao | |
| 6,503,285 B1 | 1/2003 | Murphy | |
| 6,599,334 B1 | 7/2003 | Anderson | |
| 6,645,261 B2 | 11/2003 | Murphy et al. | |
| 6,663,384 B2 | 12/2003 | Papai | |
| 6,730,137 B2 | 5/2004 | Pesu et al. | |
| 6,758,869 B2 | 7/2004 | Roeske | |
| 6,770,104 B2 | 8/2004 | Murphy | |
| 6,773,469 B2 | 8/2004 | Murphy | |
| 6,776,808 B2 | 8/2004 | Foster | |
| 6,797,020 B2 | 9/2004 | Murphy | |
| 6,824,572 B2 | 11/2004 | Murphy | |
| 6,852,140 B1 | 2/2005 | Roeske | |
| 7,018,432 B2 | 3/2006 | Moussouni | |
| 7,046,919 B2 * | 5/2006 | Shimizu | A61L 9/03 392/390 |
| 7,093,949 B2 | 8/2006 | Hart et al. | |
| 7,128,766 B2 | 10/2006 | Murphy et al. | |
| 7,133,605 B2 * | 11/2006 | Niemeyer | A61L 9/03 219/438 |
| 7,137,570 B2 | 11/2006 | Wheatley et al. | |
| 7,138,130 B2 | 11/2006 | Davis et al. | |
| 7,160,337 B2 | 1/2007 | Williams et al. | |
| 7,192,457 B2 | 3/2007 | Murphy et al. | |
| 7,217,301 B2 | 5/2007 | Murphy et al. | |
| 7,220,288 B2 | 5/2007 | D'Amico et al. | |
| 7,252,805 B2 * | 8/2007 | Hart | A01M 1/2066 122/366 |
| 7,329,839 B2 * | 2/2008 | Palmer | F21V 35/00 219/438 |
| 7,335,157 B2 | 2/2008 | Czupich et al. | |
| 7,387,649 B2 | 6/2008 | Tao | |
| 7,420,008 B2 | 9/2008 | Bloom | |
| 7,462,205 B2 | 12/2008 | Murphy | |
| 7,510,584 B2 | 3/2009 | Cap | |
| 7,569,084 B2 | 8/2009 | Tao et al. | |
| 7,588,607 B1 | 9/2009 | Cap | |
| 7,687,038 B2 | 3/2010 | Wheatley et al. | |
| 7,713,314 B2 | 5/2010 | Jones | |
| D618,329 S | 6/2010 | Koenig et al. | |
| 7,731,767 B2 | 6/2010 | Tao | |
| D621,923 S | 8/2010 | Koenig et al. | |
| 7,781,702 B2 | 8/2010 | Nam | |
| D629,051 S | 12/2010 | Nishimoto | |
| 7,959,689 B2 | 6/2011 | Cagle | |
| 8,021,443 B2 | 9/2011 | Murphy et al. | |
| 8,070,833 B2 | 12/2011 | Murphy | |
| 8,070,834 B2 | 12/2011 | Tao et al. | |
| 8,084,718 B1 | 12/2011 | Shotey et al. | |
| 8,364,028 B1 * | 1/2013 | Vaske | A61L 9/03 219/385 |
| 8,371,740 B2 | 2/2013 | Pestl et al. | |
| 8,496,881 B2 | 7/2013 | Pohl et al. | |
| D694,382 S | 11/2013 | Brandenburg et al. | |
| 2001/0001282 A1 | 5/2001 | Parmentier et al. | |
| 2003/0007887 A1 | 1/2003 | Roumpos et al. | |
| 2005/0016985 A1 * | 1/2005 | Haas | A61L 9/03 219/438 |
| 2005/0169666 A1 * | 8/2005 | Porchia | A01M 1/02 399/111 |
| 2006/0219694 A1 | 10/2006 | Wu | |
| 2006/0272199 A1 | 12/2006 | Licciardello et al. | |
| 2007/0031298 A1 * | 2/2007 | Roumpos | A61L 9/02 422/125 |
| 2007/0282000 A1 | 12/2007 | Murphy et al. | |
| 2008/0130266 A1 * | 6/2008 | DeWitt | A61L 9/03 362/96 |
| 2008/0138753 A1 | 6/2008 | Tao et al. | |
| 2008/0282601 A1 | 11/2008 | Luttke | |
| 2009/0217568 A1 | 9/2009 | Murphy et al. | |
| 2010/0024281 A1 | 2/2010 | Lemke et al. | |
| 2010/0044924 A1 | 2/2010 | Cap | |
| 2010/0096376 A1 * | 4/2010 | Hsiao | A61L 9/03 219/201 |
| 2010/0205851 A1 | 8/2010 | Uptain et al. | |
| 2010/0264232 A1 | 10/2010 | Gruenbacher et al. | |
| 2010/0308126 A1 | 12/2010 | Gruenbacher et al. | |
| 2011/0110072 A1 * | 5/2011 | Hsiao | A61L 9/03 362/96 |
| 2011/0110824 A1 * | 5/2011 | Hsiao | A61L 9/035 422/125 |
| 2012/0024837 A1 * | 2/2012 | Thompson | A61L 9/03 219/433 |
| 2012/0183280 A1 * | 7/2012 | Kowalec | A61L 9/03 392/386 |
| 2012/0318779 A1 * | 12/2012 | Juarez | H01R 33/22 219/209 |
| 2013/0020307 A1 * | 1/2013 | Ashton | H05B 3/68 219/387 |
| 2013/0170184 A1 * | 7/2013 | Browder | A61L 9/015 362/96 |
| 2014/0017136 A1 | 1/2014 | Wirz | |
| 2015/0174278 A1 * | 6/2015 | Belongia | A61L 9/03 392/386 |
| 2015/0283280 A1 * | 10/2015 | Belongia | A61L 9/03 392/386 |
| 2015/0305089 A1 * | 10/2015 | Belongia | H05B 3/0052 219/438 |

OTHER PUBLICATIONS

First Office Action issued in corresponding Chinese Application No. 201580026363.5, dated Dec. 25, 2018, 17 pages.

* cited by examiner

US 10,363,333 B2

WAX WARMER

CROSS REFERENCE TO RELATED APPLICATIONS

Not applicable

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present disclosure generally relates to a wax warmer, and more specifically, to a wax warmer for use with a wax melt to dispense materials into the surrounding environment.

2. Description of the Background of the Invention

Wax melts can be placed in an electric wax warmer to provide pleasant aromas without an open flame. Many electric wax warmers known in the art also provide a source of illumination. Electric wax warmers may also be used to provide more than just illumination and/or pleasant fragrances. For instance, the wax may include materials with insect repellant properties and be placed outside on a patio or deck. Generally, users can warm waxes to provide desired effects to the surrounding atmosphere or environment.

Traditional electric wax warmers may have some drawbacks. The manufacture and assembly of an electric wax warmer may be complicated and costly. Also, while electric wax warmers are available in a large variety of styles to satisfy many different aesthetic tastes of consumers, they are not customizable or easily updated. Owning a large variety of differently decorated electric wax warmers to display seasonally or to freshen a room's decor is inconvenient and expensive. Also, if any of the components of an electric wax warmer are damaged or worn out, the entire unit needs to be replaced.

Therefore, there is a need for an electric wax warmer that overcomes the aforementioned drawbacks. In particular, there is a need for a wax warmer that provides superior wax warming performance while providing flexibility in manufacturing and assembly. Further, there is a need for an electric wax warmer that provides an easy and efficient means for replacing any damaged or worn out components. Further still, there is a need for an electric wax warmer that is easy to customize to a satisfy a user's unique style and decor demands.

The present disclosure overcomes some of the aforementioned drawbacks by providing a wax warmer that maintains excellent wax melting performance while being easy and inexpensive to manufacture and customize. Further, the wax warmer disclosed herein also makes possible the replacement of any worn or damaged components by the user through minimal expense and effort.

SUMMARY OF THE INVENTION

According to one aspect, a wax warmer includes a reservoir module for receiving a wax melt, a heater module, and a base module. The heater module includes a heating element. The reservoir module, the heater module, and the base module are removable from one another in the normal use of the wax warmer and may be replaced by a second reservoir module, a second heater module, or a second base module, respectively.

According to another aspect, a method of providing a wax warming system includes providing a wax warmer that includes a first reservoir module, a first heater module, and a first base module. The first reservoir module, the first heater module, and the first base module are interchangeable. The method also includes the steps of providing at least one wax melt and providing written instructions that inform a user how to operate the wax warmer. The instructions include at least one or more of the following steps of instructing the user to replace the first base module with a second base module, instructing the user to replace the first heater module with a second heater module, and instructing the user to replace the first reservoir module with a second reservoir module.

According to a further aspect, a wax warmer includes a reservoir module having a wax melt secured thereto, a heater module including a heating element, and a base module. The heater module is retained on an upper end of the base module. The reservoir module is releasably retained on an upper end of the heater module. A user may release the reservoir module from the heater module to replace the reservoir module in normal use of the wax warmer.

BRIEF DESCRIPTION OF THE DRAWINGS

Other aspects and advantages of the present invention will become apparent upon consideration of the following detailed description, wherein similar structures have similar reference numerals.

DETAILED DESCRIPTION

Figure 1:
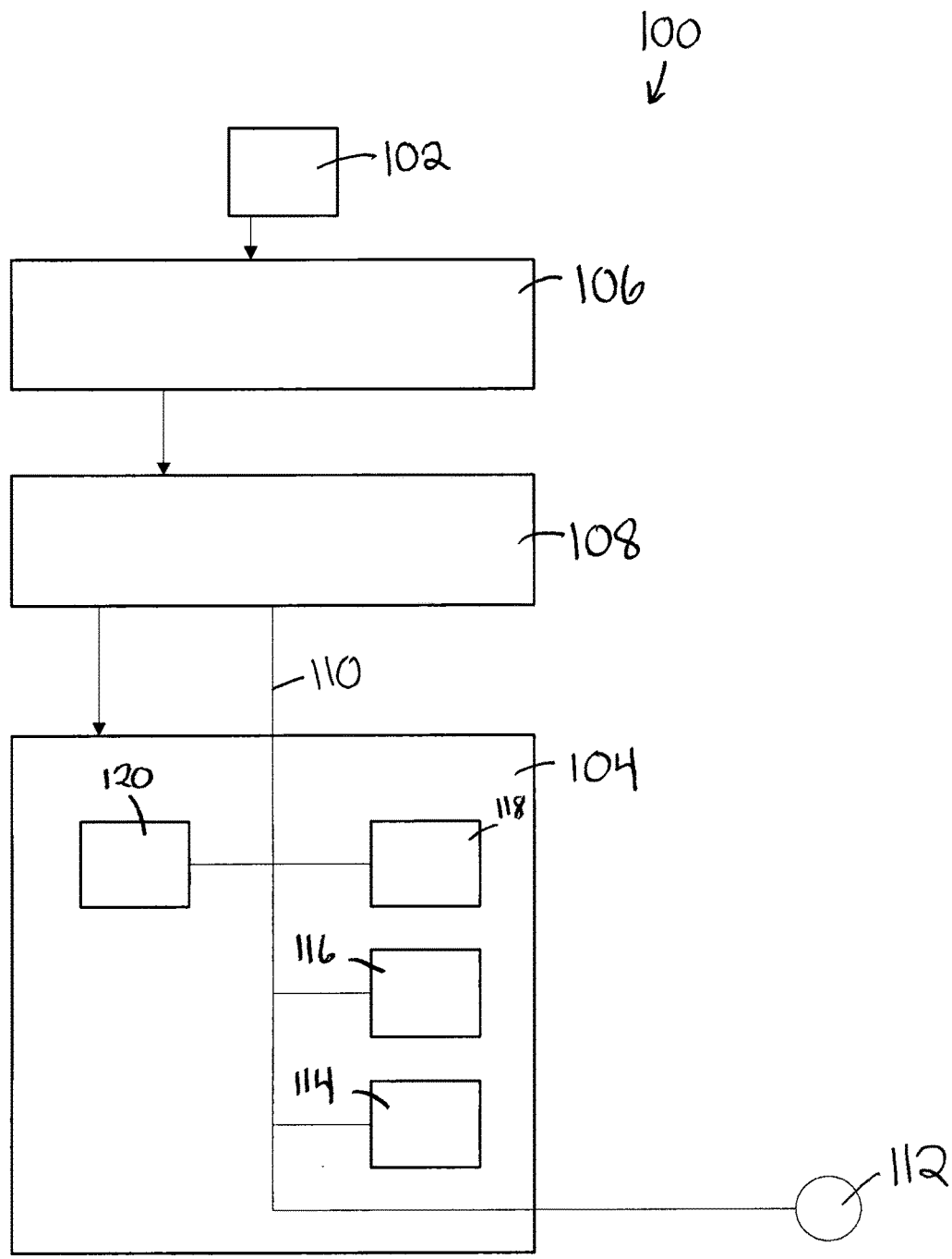
FIG. 1 is a schematic depiction of a wax warmer with a wax melt.

Referring to FIG. 1, a schematic representation of a wax warmer 100 is depicted. The wax warmer 100 is designed to heat a wax melt 102 and thereby release a fragrance or other volatile material contained therein into the surrounding environment. The wax warmer 100 generally includes three modules, which comprise a base module 104, a reservoir module 106, and a heater module 108. The modules 104, 106, 108 are constructed such that the base module 104 supports the heater module 108 and the heater module 108 supports the reservoir module 106 during normal operation (see arrows in FIG. 1). The heater module 108 includes an electrical cord 110 for providing electrical power to the heater module 108. The electrical cord 110 may pass through the base module 104 to connect to an electrical outlet 112. In some embodiments the cord 110 may connect to the heater module 108 with a plug (not shown) adapted to mate with a socket (not shown) on the heater module 108. In other embodiments the cord 110 may be permanently attached to the heater module 108. Another alternative embodiment may include batteries (not shown) to provide electrical power to the heater module 108.

Figure 2:
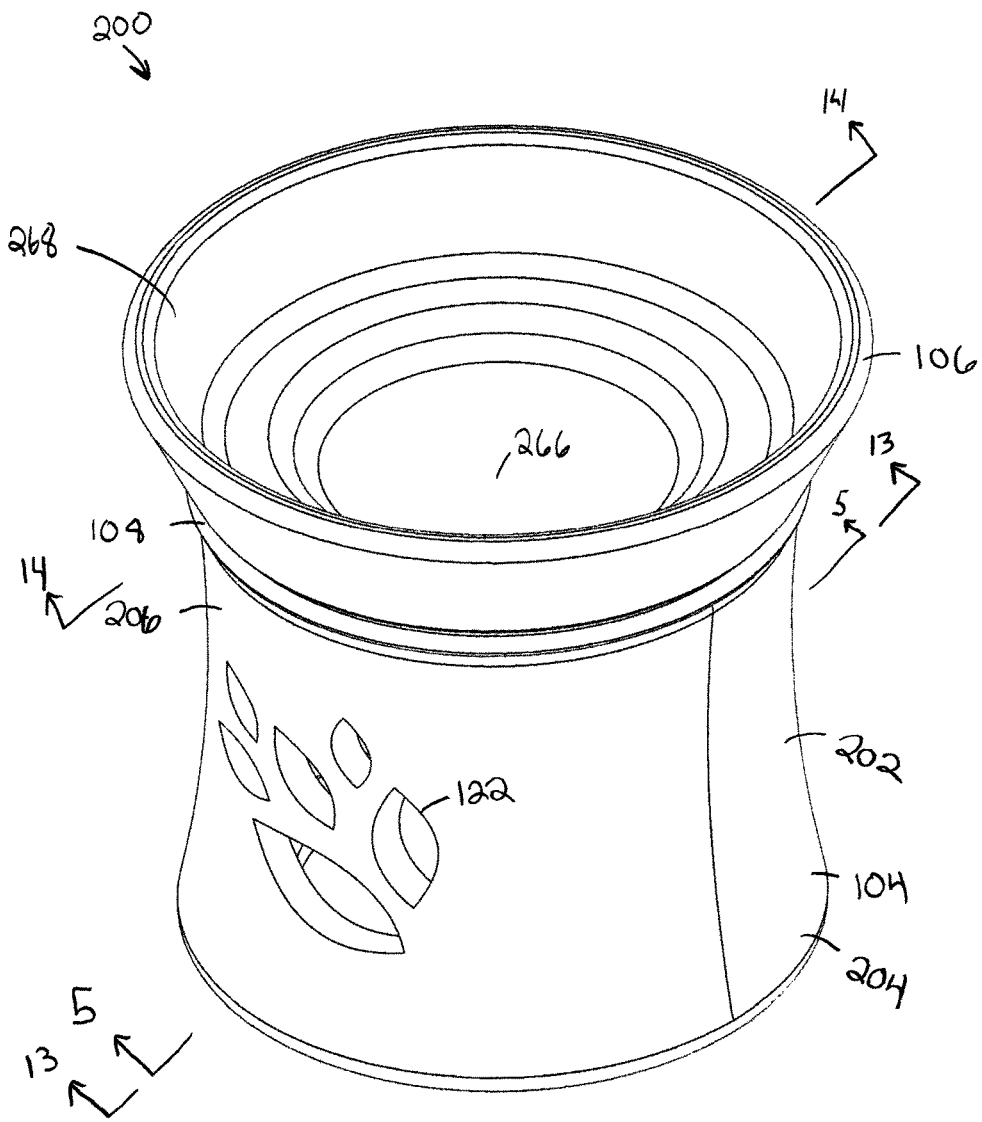
FIG. 2 is a top and front isometric view of a wax warmer.
Figure 3:
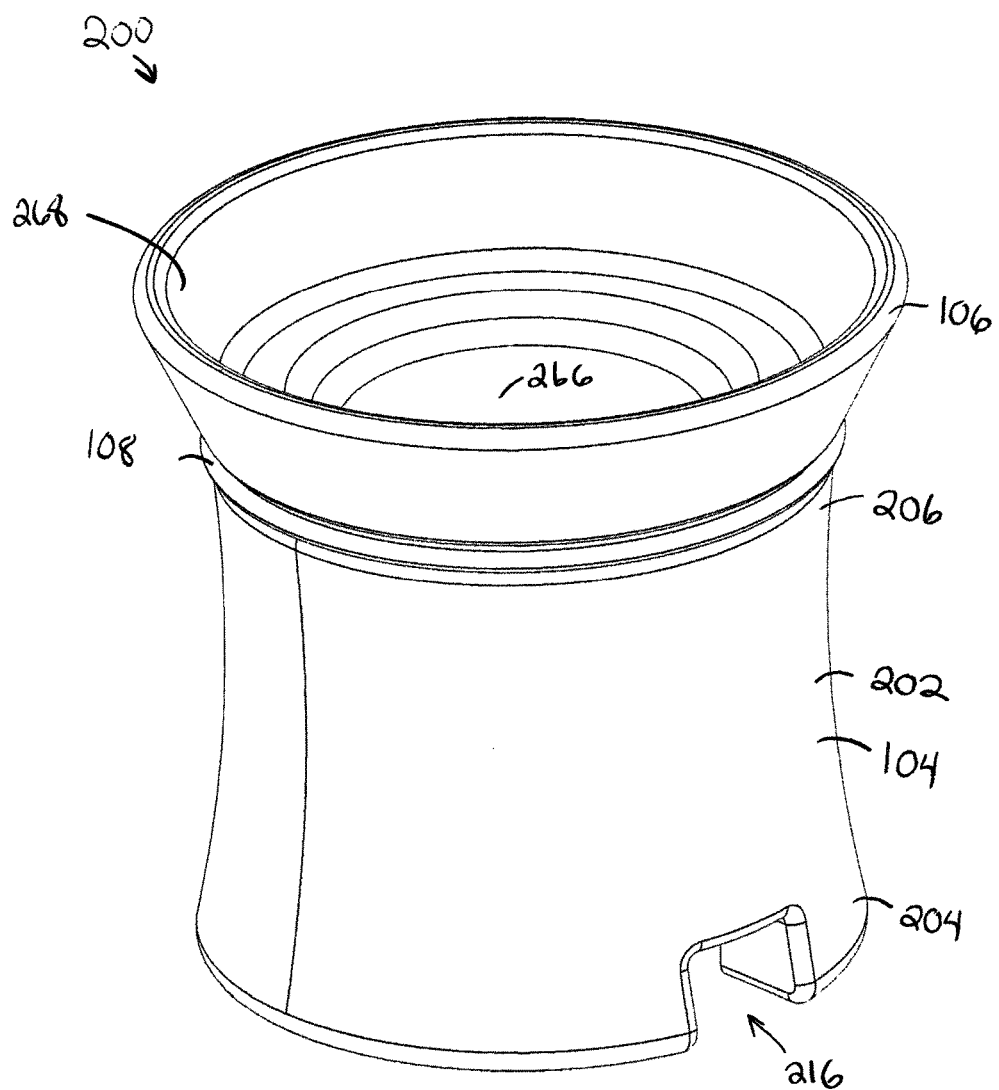
FIG. 3 is a top and rear isometric view of the wax warmer of FIG. 2.

It is contemplated that the cord 110 may include a switch 114 and/or a control module 116 in some embodiments. The control module 116 and the switch 114 may be inline components of the cord 110 such that they are external to the base module 104 and accessible by a user when the wax warmer 100 is configured for normal operation. Alternatively, the base module 104 may include support structure (not shown) for the switch 114 and the control module 116 to be retained within the base module 104 and accessed by the user through apertures (not shown) in the base module 104 or otherwise mounted to a sidewall thereof. It is also contemplated that the wax warmer 100 may include sensors 118. The control module 116 may receive signals for the sensors 118 and include the capability to be programmed by the user for different modes of operation. The sensors 118 may be mounted on the cord 110 or they may be mounted on the base module 104. The cord 110 may also include one or more light emitting diodes (LEDs) 120 as an inline component. The LEDs 120 may provide indication to the user that the wax warmer 100 is operational, is inoperational, is in a standby mode, is in a lockout mode, is detecting sensory input, has detected sensory input, etc. Alternatively, the LEDs 120 may provide illumination for aesthetic purposes or some other functional purpose as would be known to one of ordinary skill. In some embodiments, the LEDs 120 may be viewed through apertures 122 (See FIG. 2) in the base module 104. The LEDs 120 may be part of the control module 116 and/or the switch 114.

Figure 1A:
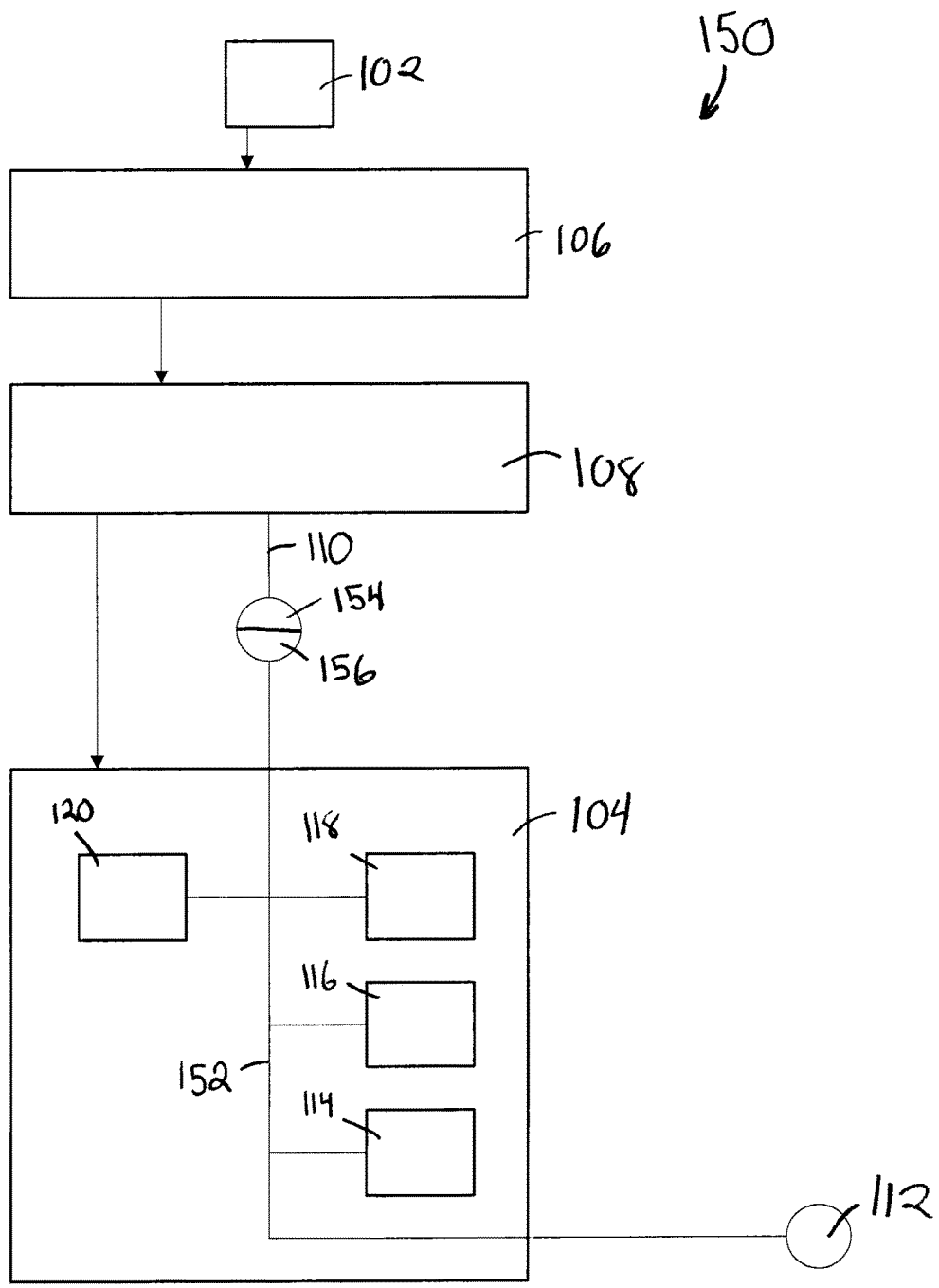
FIG. 1A is schematic depiction of another embodiment of a wax warmer with a wax melt.

Now turning to FIG. 1A, another schematic embodiment of a wax warmer 150 is depicted. The wax warmer 150 may include a wiring harness 152 or other internal electrical structure mounted in the base module 104 that may include one or more of the LEDs 118, the control module 116, and the switch 114 as described above. The cord 110 may include a plug 154 that mates with a socket 156 of the wiring harness. The wiring harness 152 thereby provides electrical power to the heater module 108 and other electrical components through a connection to the external electrical outlet 112.

Referring to FIGS. 1 and 1A, the wax warmers 100, 150 are contemplated to be modular in nature. The reservoir module 106, the heater module 108, and the base module 104 are therefore reconfigurable or replaceable during the normal operation of the wax warmers 100, 150. Normal operation of the wax warmers 100, 150 comprises the time and actions taken by a user in assembling and/or configuring the wax warmer 100, 150 through manipulation of the modules 104, 106, 108 to utilize the wax warmer 100, 150 to warm the wax melt 102. Normal operation would also include the time and actions taken by the user in reconfiguring the wax warmer 100, 150 by replacing one or more of the modules 104, 106, 108 with a replacement module 104, 106, 108. Normal operation does not include a manufacturing step upstream of a use by an end user of the wax warmer 100, 150. Normal use also constitutes a point in time when tools, besides manual manipulation by the user, are no longer required to assemble or configure the wax warmer 100, 150 and/or any replacement module 104, 106, 108. The user may purchase the reservoir module 106, the heater module 108, and the base module 104 together as a starter kit or, alternatively, may purchase or otherwise procure one or more of the reservoir module 106, heater module 108 or base module 104 separately. For a user to enjoy the modular nature of the wax warmer 100, no special skills should be required to configure and reconfigure the unit for normal operation. The process (to be described in detail later) of retaining the reservoir module 106, the heater module 108, and the base module 104 in a normal operational configuration is preferably easy for a layperson to accomplish.

Referring to FIGS. 2-5, another embodiment of a wax warmer 200 is depicted, which may encompass any of the structure or operational characteristics of the wax warmers 100, 150. Common elements shared between the embodiments in the present application will share the same numbers. The wax warmer 200 includes a base module 104, a reservoir module 106, and a heater module 108. The base module 104 is fashioned to house the heater module 108 and provide a support structure for the reservoir module 106. The wax warmer 200 is generally described to include the aforementioned components, but the wax warmer 200 may be adapted to add or remove various components according to specific user requirements.

Figure 4:
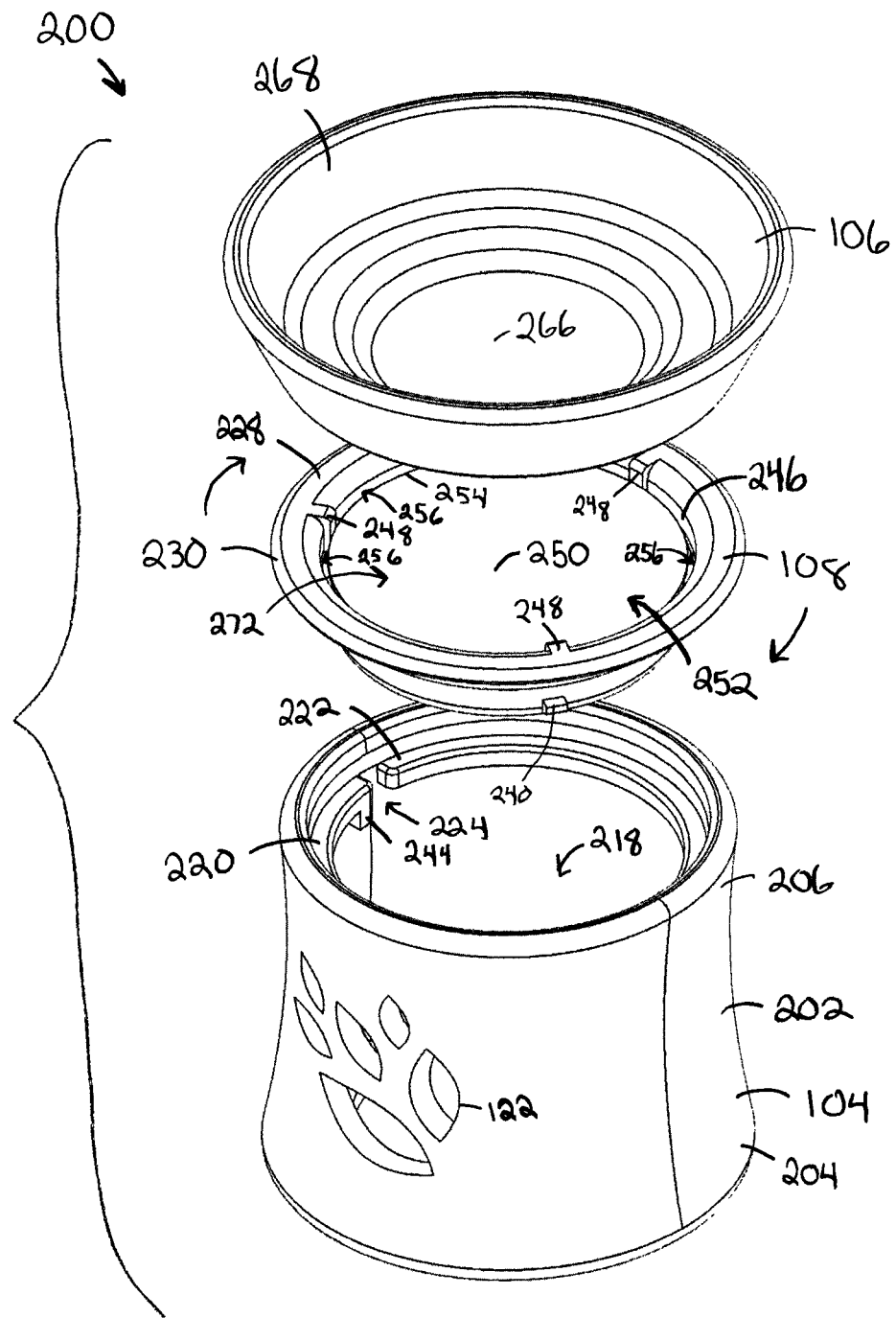
FIG. 4 is an exploded isometric view of the wax warmer of FIG. 2.
Figure 5:
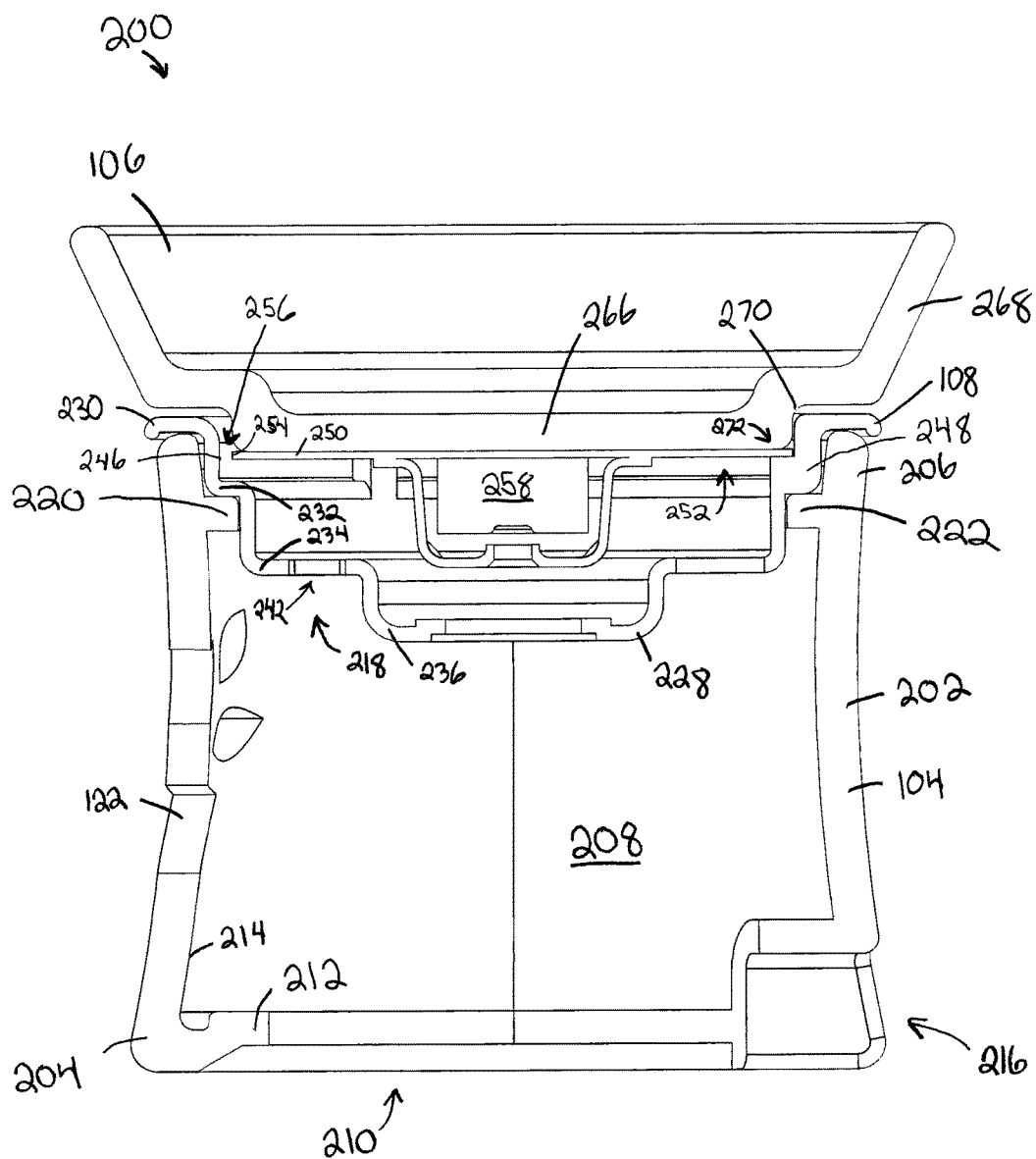
FIG. 5 is a cross-sectional view of the wax warmer of FIG. 2 taken generally along the line 5-5 of FIG. 2.

With respect to FIGS. 4 and 5, the base module 104 includes a sidewall 202 having a bottom end 204 and a top end 206. In the present embodiment, the sidewall 202 is generally cylindrical in shape and defines an inner space 208 (see FIG. 5). The bottom end 204 defines a first opening 210. A lip 212 extends from an inner surface 214 of the sidewall 202 adjacent the bottom end 204. The bottom end 204 or the lip 212 may include extensions (not shown) or other structures (e.g., feet, pads, elements with high coefficients of friction, etc.) generally known to those having ordinary skill in the art to provide stability to the wax warmer 200. A cord aperture 216 (see FIGS. 3 and 5) is also provided proximal to the bottom end 204 of the sidewall 202. Preferably, the cord aperture 216 provides a pass-through for an electrical cord (not shown) in electrical communication with the heater module 108 and other electrical components.

Figure 6:
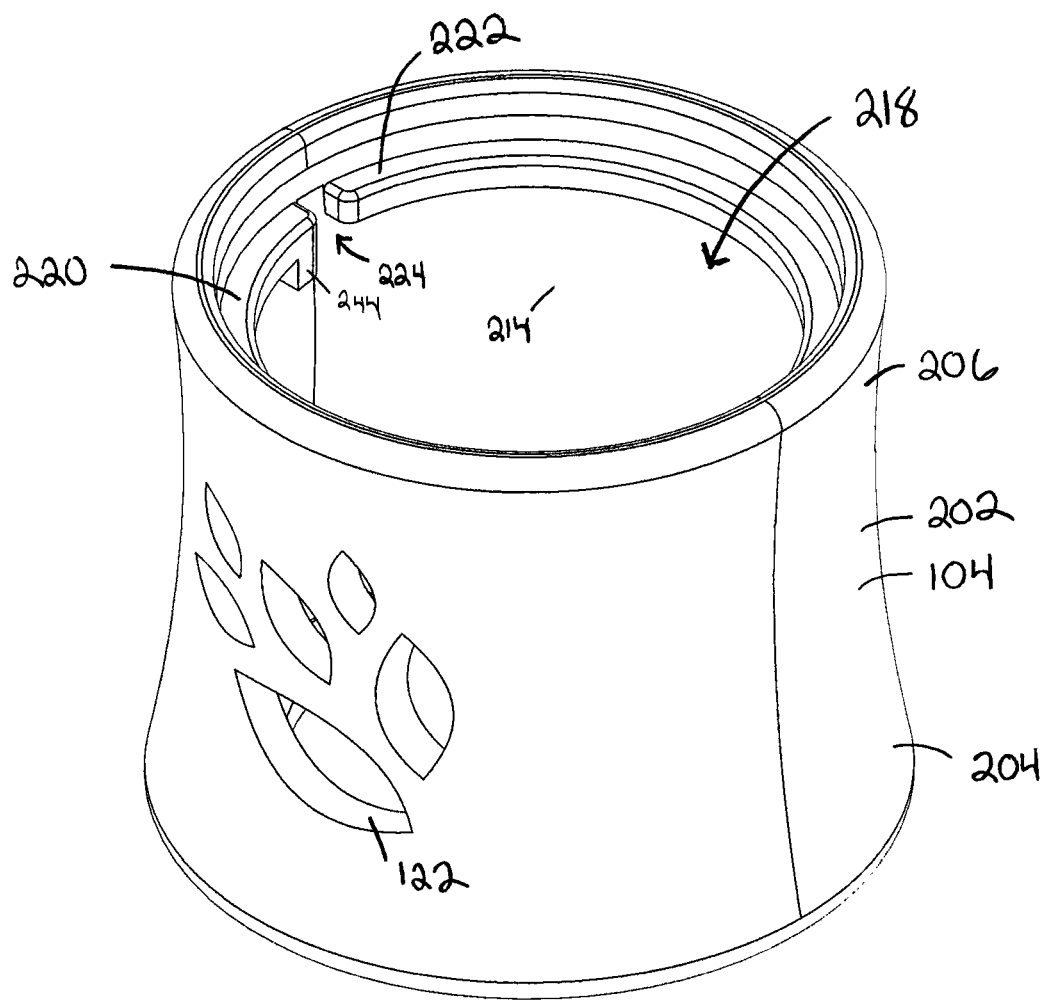
FIG. 6 is a top, front, and right side isometric view of a base of the wax warmer of FIG. 2.
Figure 7:
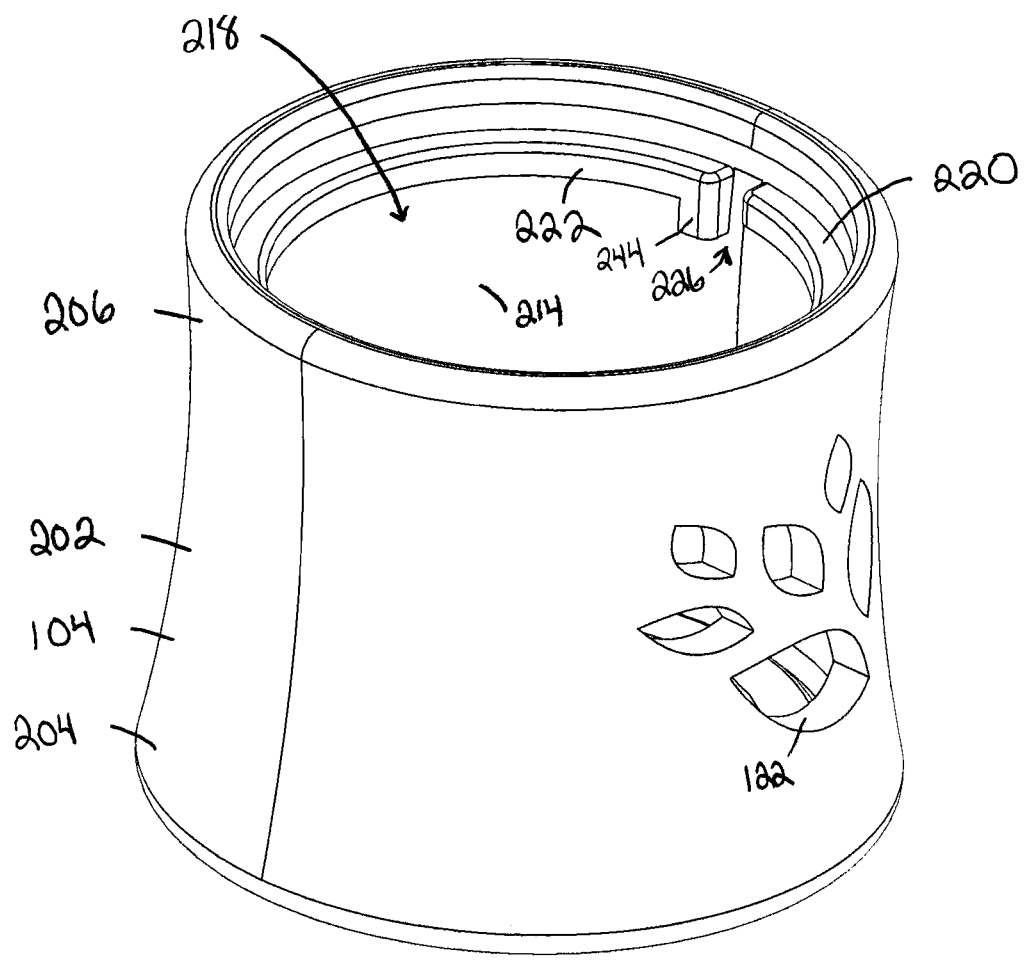
FIG. 7 is a top, front, and left side isometric view of a base of the wax warmer of FIG. 2.
Figure 8:
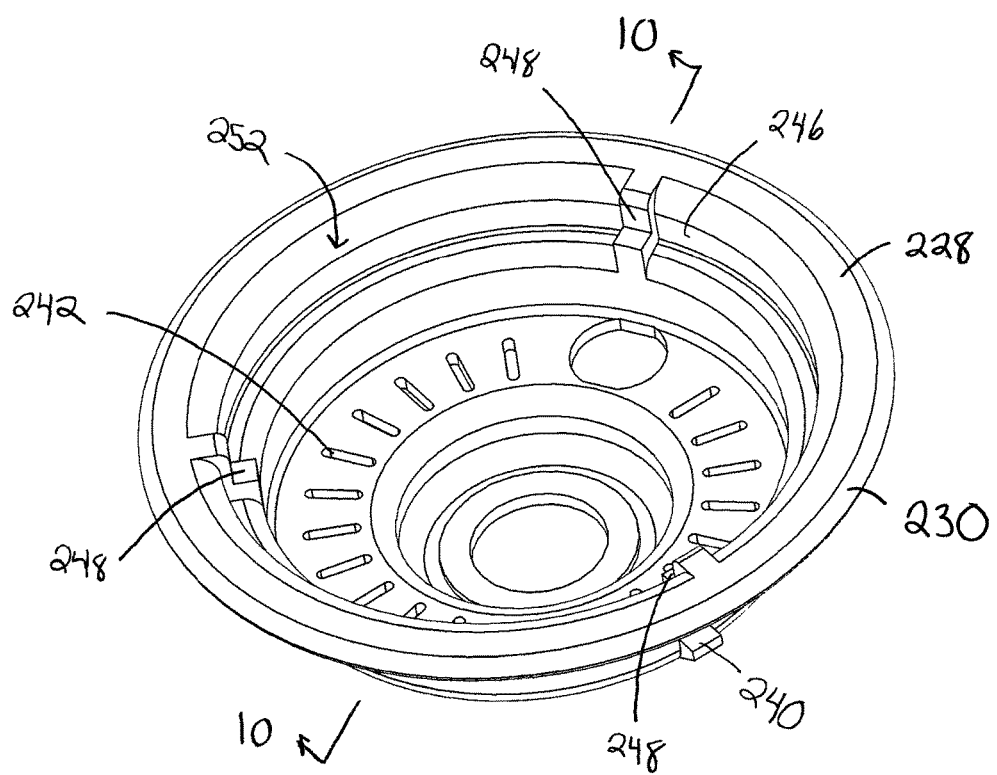
FIG. 8 is a top and front isometric view of a heater module housing of the wax warmer of FIG. 2.
Figure 9:
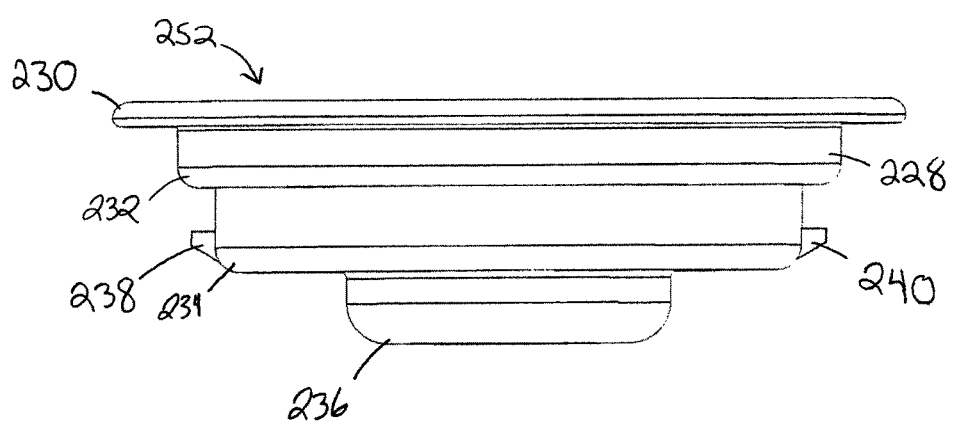
FIG. 9 is a side elevational view of the heater module housing of FIG. 8.
Figure 10:
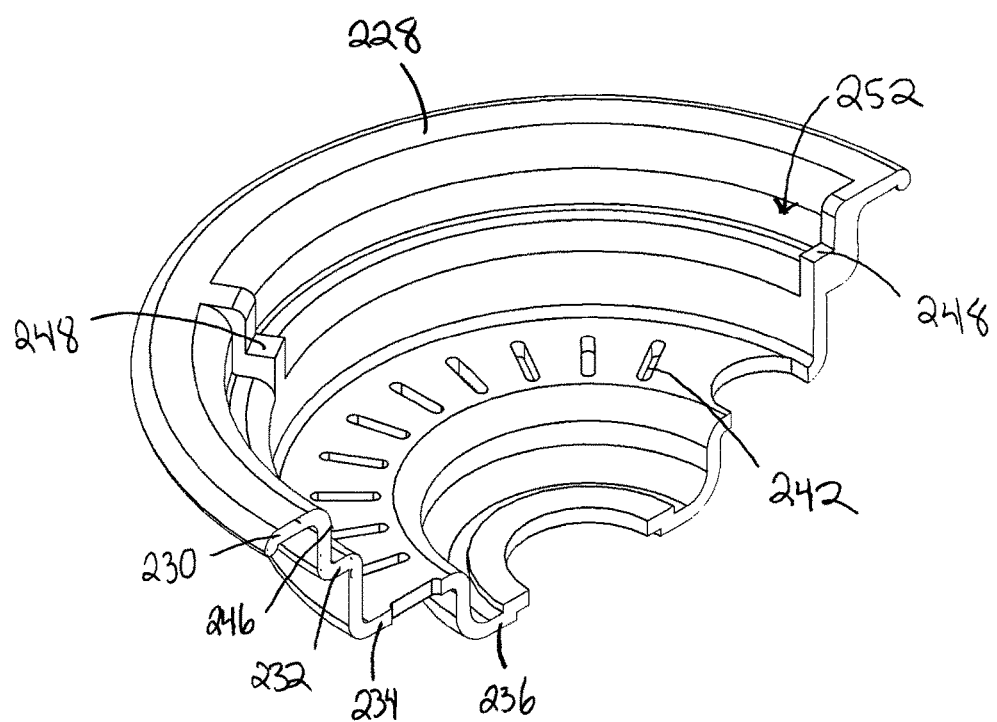
FIG. 10 is a cross-sectional view of the heater module housing of FIG. 8 taken generally along the line 10-10 of FIG. 8.
Figure 11:
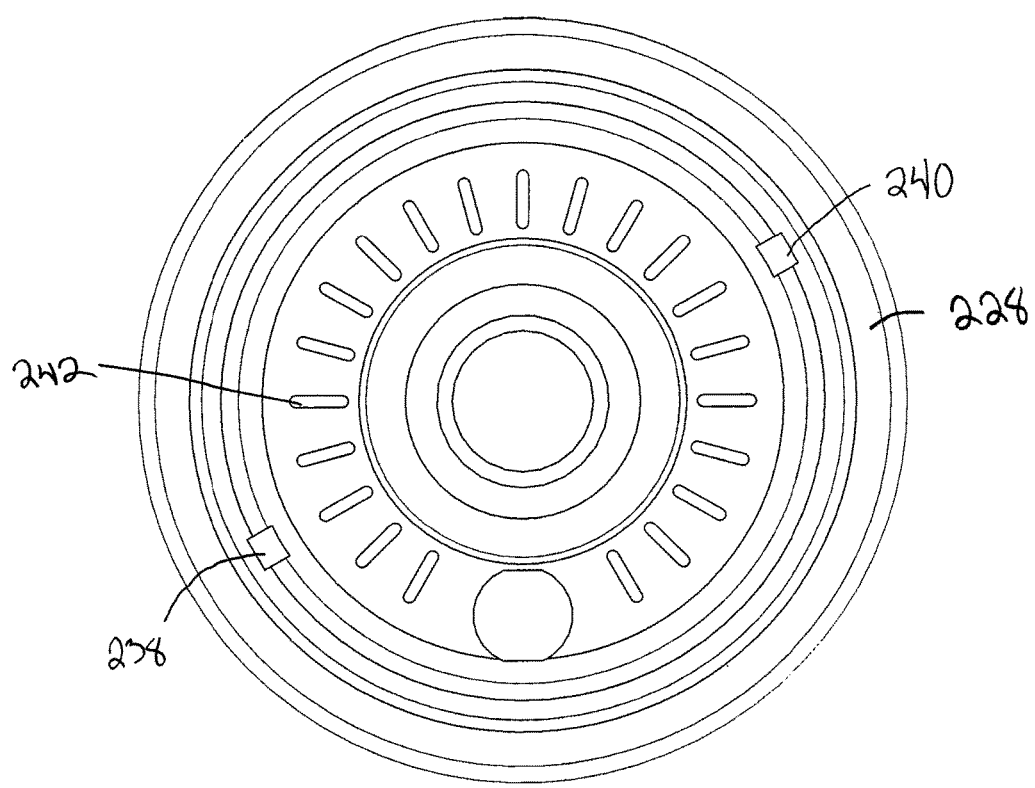
FIG. 11 is a bottom elevational view of the heater module housing of FIG. 8.

Turning again to FIGS. 4-7, a second opening 218 is provided at the top end 206 of the sidewall 202. A first flange 220 and a second flange 222 extend from the inner surface 214 of the sidewall 202 proximal to the top end 206. A first gap 224 and a second gap 226 are defined by the first flange 220 and the second flange 222 (see FIGS. 6 and 7). The second opening 218 and the first and second flanges 220, 222 and the first and second gaps 224, 226 are adapted to receive the heater module 108.

With reference to FIGS. 8-11, the heater module 108 includes a housing 228. The housing 228 forms a cup-like structure with three annular sections extending downward from a U-shaped lip 230. The housing 228 includes a first section 232, a second section 234, and a third section 236. A first lug 238 and a second lug 240 extend radially outward from the second section 234. The second section also includes inlet vents 242. In the present embodiment, the inlet vents 242 are oval shaped apertures.

The heater module 108 is adapted to be retained within the top end 206 of the sidewall 202 of the base module 104. Specifically, the U-shaped lip 230 and the first section 232 are adapted to be retained by the top end 206 of the sidewall 202 and the flanges 220, 222, respectively. During placement of the heater module 108 into the first opening 218, the first and second lugs 238, 240 are sized to pass through the first and second gaps 224, 226. The user must align the lugs 238, 240 with the gaps 224, 226 to insert the heater module 108 into the base module 104. After insertion, the lugs 238, 240 are below the level of the flanges 220, 222. The user thereafter rotates the heater module 108 until the lugs 238, 240 contact stops 244 (see FIGS. 6 and 7) extending downward from the flanges 220, 222. It is also contemplated that the releasable structure of the modules of the wax warmer 200 described above may take other forms. For example, the arrangement between the lugs 238, 240 of the heater module 108 and the flanges 220, 222 and gaps 224, 226 may be replaced with a threaded structure (not shown).

Turning again to FIGS. 8 and 10, an inner surface 246 of the first section 232 includes three spacer projections 248. Now referring to FIG. 5, a heating plate 250 is supported in an upper opening 252 defined by the inner surface 246 and the spacer projections 248. It is contemplated that the heating plate 250 may be made of metal. Alternatively, the heating plate may be made of any other materials (e.g., high temperature plastics) known to one having skill in the art that may provide adequate thermal transfer. The heating plate 250 is supported by the spacer projections 248 such that a circumferential edge 254 of the heating plate 250 is spaced apart from the inner surface 246 of the housing 228 except where contact is made with the spacer projections 248. This arrangement forms outlet vents 256 between the circumferential edge 254 of the heating plate 250 and the inner surface 246 of the housing 228. The heating plate 250 is in thermal contact with a heating element 258 within the housing 228 of the heater module 108. The heating plate 250, the heating element 258, and the housing 228 may be secured together by known means. For clarity, the electrical and mechanical structure within the heating module and the electrical cord to provide electrical power have been excluded from the figures.

Figure 12:
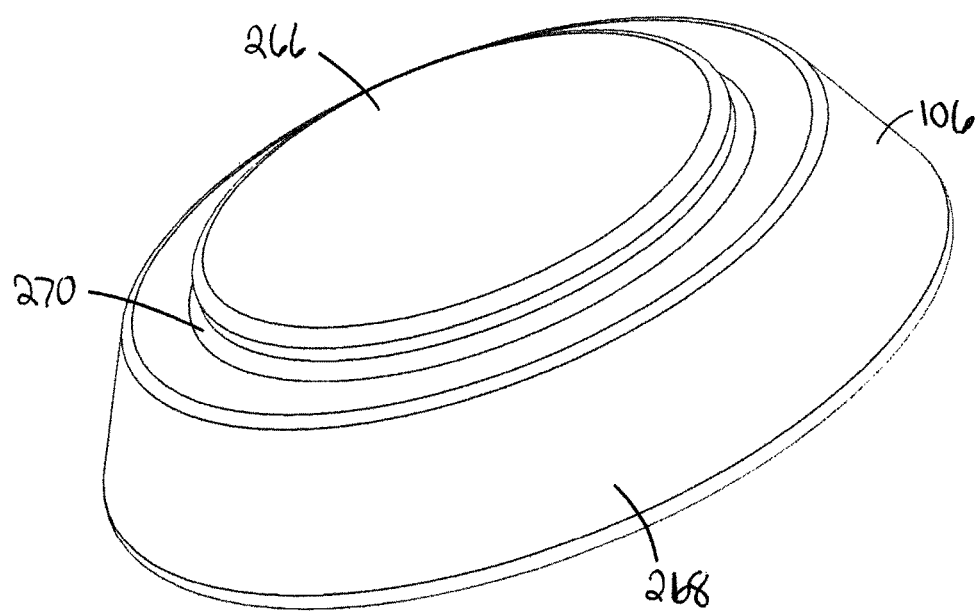
FIG. 12 is a bottom isometric view of a reservoir of the wax warmer of FIG. 2.

Turning to FIGS. 4, 5, and 12, the reservoir module 106 includes a lower cylindrical projection comprising a bottom wall 266. The bottom wall 266 and the sidewall 268 form a cup-like structure for containing the wax melt 102 in a pre-operative solid state and in an operative state when the wax melt 102 is in a liquid or semi-liquid state. The reservoir module 106 further includes an annular cut-out 270. When the heating plate 250 rests on the spacer projections 248 of the heater module housing 228, the plate 250 and the inner surface 246 of the housing 228 define a recess 272. The recess 272 is configured to receive the cylindrical projection of the bottom wall 266 of the reservoir module 106. Further, the cut-out 270 of the reservoir module 106 is adapted to receive an interior portion of the U-shaped lip 230 of the heater module housing 228. The interaction of the U-shaped lip 228 with surfaces defining the cut-out 270 and the cylindrical projection of the bottom wall 266 with surfaces defining the recess 272 retain the reservoir module 106 on the heater module 108.

The bottom wall 266 of the reservoir module 106 is generally flat to provide maximum thermal contact with the heating plate 250. The present arrangement also ensures that the reservoir module 106 is centered on the heater module 108 for improved thermal transfer from the heating element 258 to the wax melt 102. Also, the reservoir module 106 may be easily replaced with another reservoir (not shown) that has the same structural characteristics but a different aesthetic design.

Figure 13:
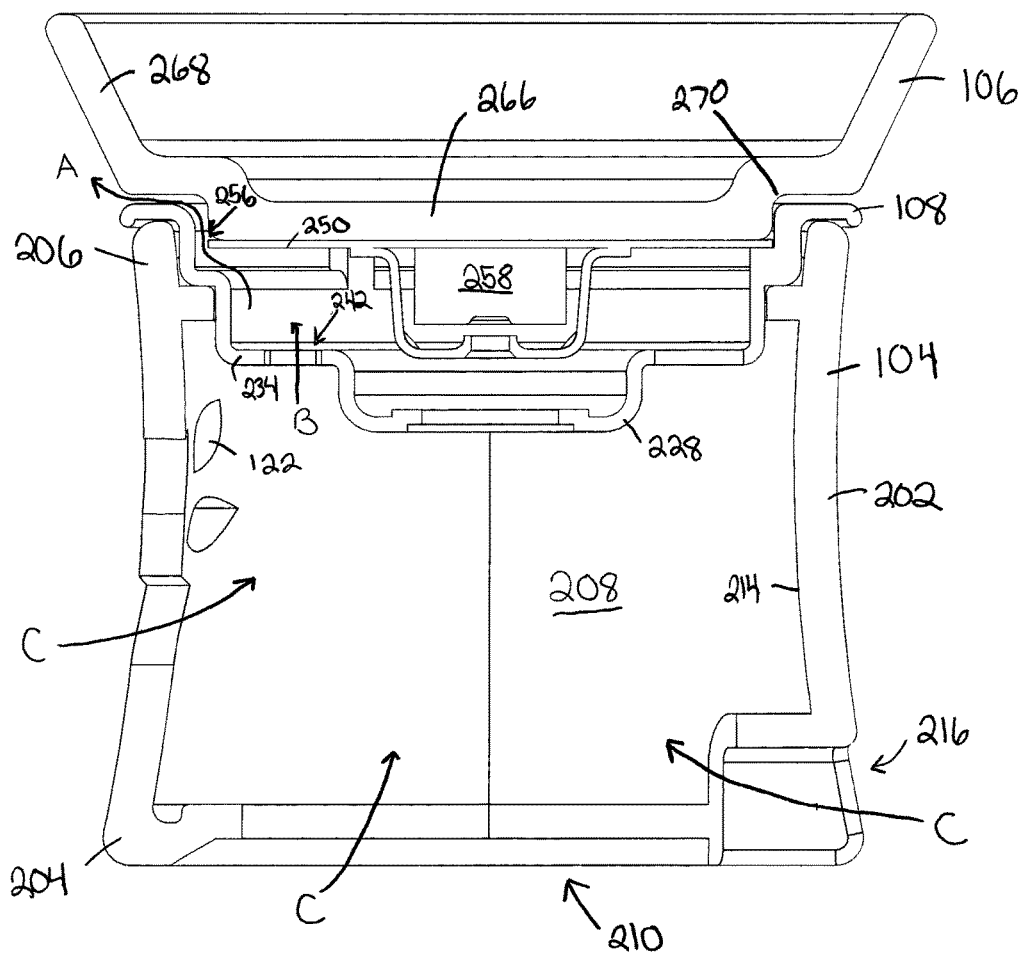
FIG. 13 is a cross-sectional view of the wax warmer of FIG. 2 taken generally along the line 13-13 of FIG. 2 depicting the air flow through the wax warmer.

Referring to FIG. 13, during operation the heating element 258 heats the wax melt 102 in the reservoir module 106 through heat transferred through the heating plate 250 and the bottom wall 266. Some heat will also be transferred to the air within the heating module 108. The heated air will rise up through the outlet vents 256 and up the sidewall 268 of the reservoir module 106 (see the arrow A). As the heated air rises out of the heater module 108, cooler air from the inner space 208 will be drawn up into the heater module 108 through the inlet vents 242 of the second section 234 of the housing 228 (see the arrow B). Air may be drawn into the inner space 208 of the base module 104 through any of the apertures 122, the cord aperture 216, or the first opening 210 of the base (see the arrow C). Thus, while the heating element 258 is operational, a flow of air from outside the base module 104, through the inner space 208 and the heater module 108, and up past the reservoir module 106 into the surrounding environment will be created. This flow of air may help with the distribution of fragrance or volatile material from the wax melt 102 and may also help prevent the heating element 258 from overheating.

It has been contemplated that the base module 104 and the reservoir module 106 are preferably made from a ceramic material. However, any other materials as known to those having ordinary skill in the art may be used, such as plastic, metal, stone or other natural materials. The base module 104, the reservoir module 106, and the heater module 108 may take any geometric shape, e.g. a cylinder or square, to provide different appearances. Further, the exterior surfaces of the base module 104 and the reservoir module 106 may be provided with any type of surface indicia, raised patterns, or any other decorations to configure the wax warmer 100 for aesthetic purposes.

In the preferred embodiment shown in the figures, the heating element 258 is a resistive type heater. However, it is contemplated that the heater may be any type of heater, for example, the heater may be a positive thermal coefficient heater or an inductive type heater. It is further contemplated that the heating element 258 may be replaced by a series of heaters or any known heating arrangement that allows the heating element 258 to make sufficient thermal contact with the heating plate 250.

The wax melt 102 is wickless and may comprise any geometric shape. In one preferred embodiment, the wax melt 102 has a generally square shape with slightly rounded curvature imparted thereto at an area where sidewalls of the wax melt intersect with each other. There are no substantial surface interruptions beyond minor surface irregularities formed during the manufacturing process. It is contemplated that the shape of the wax melt 102 may be configured to be beneficial for manufacturing purposes or aesthetic reasons or both.

Figure 14:
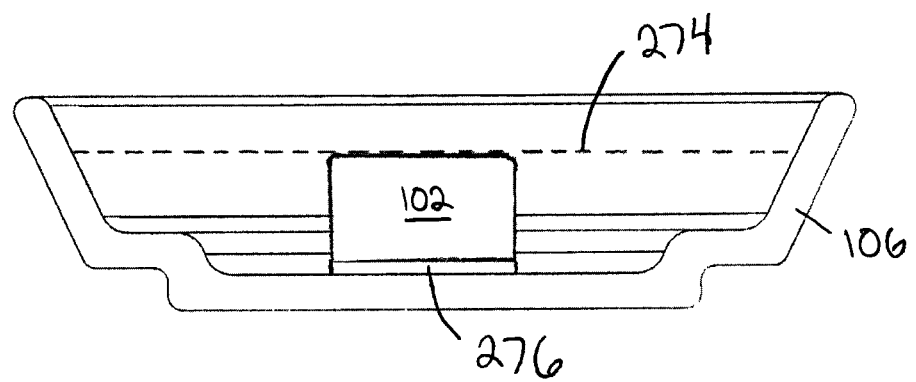
FIG. 14 is a cross-sectional view of a reservoir module of the wax warmer of FIG. 2 taken generally along the line 14-14 of FIG. 2.

It is also envisioned that the wax melt 102 may be secured to the reservoir module 106 prior to normal use by the user. For example, the reservoir module 106 may be purchased as part of a kit or an individual item that includes the wax melt 102. It is considered that the wax melt 102 may be wrapped, e.g., in a plastic or malleable material, with the reservoir module 106, or secured by way of a blister cartridge or shell that retains and secures the reservoir module 106 with the wax melt 102 (see for example 274 in FIG. 14). In one embodiment, the wax melt 102 is irremovably attached to the reservoir module 106 prior to purchase by the user and prior to melting of the wax melt 102 during normal use of the wax warmer 200. Several non-exhaustive securing mechanisms (see for example 276) include an adhesive, a chemical bond between the wax melt 102 and a surface of the reservoir module 106, an interference fit between surfaces of the wax melt 102 and surfaces of the reservoir module 106, and a projection extending from the reservoir module 106 into the wax melt 102. In embodiments utilizing a wax melt 102 secured to the reservoir module 106, it is further contemplated that the reservoir module 106 alone may be removable and replaceable with a second reservoir module 106. However, it is also anticipated that any of the components of the wax warmer 200 may be interchangeably removable as previously described.

It is also contemplated that the wax warmer 200 may be part of a kit that may include one or more wax melts 102, the base module 104, the reservoir module 106, the heater module 108, and instructions for the assembly and use thereof. The user may purchase the kit and possibly one or more replacement modules. The instructions may include the steps of removing the modules 104, 106, 108 and the wax melt 102 from any packaging materials; assembling the wax warmer 200 by placing the heater module 108 on the base module 104 and the reservoir module 106 on the heater module 108; making any required electrical connections; placing a wax melt within the reservoir 106; switching on the wax warmer 200; turning off the wax warmer 200; replacing the wax melt 102 or adding additional wax melts 102; changing from one type of wax melt 102 to another different type of wax melt 102; instructing the user on proper safety precautions; and reconfiguring and/or disassembling the wax warmer 200.

The instructions may include instructing the user to replace at least one of a first base module 104, a first reservoir module 106, and a first heater module 108 with a second base module 104, a second reservoir module 106, and a second heater module 108. The user may replace any of the modules 104, 106, 108 for the purpose of customizing the wax warmer 200 or replacement of a worn or damaged module 104, 106, 108. Normal use of the wax warmer 200 may include configuring and reconfiguring the wax warmer 200.

From the description above it is contemplated that several manufacturing advantages should be apparent. First, the wax warmer 200 does not require only a single supplier to manufacture all the components. For example, a ceramic supplier may manufacture the base module 104 and the reservoir module 106, while a separate manufacturer may be used for the heater module 108. Second, complex assembly steps have been reduced or eliminated through the use of the provided modules 104, 106, 108. Third, the flexibility provided to the manufacturer in designing and building the wax warmer 200 allows for much greater flexibility for the customer to customize the wax warmer.

Any of the embodiments described herein may be modified to include any of the structures or methodologies disclosed in connection with different embodiments. Further, the present disclosure is not limited to wax warmers of the type specifically shown. Still further, the wax warmers of any of the embodiments disclosed herein may be modified to work with any type of warmer that utilizes wax melts or the like.

INDUSTRIAL APPLICABILITY

A wax warmer is presented that heats a wax melt for dispensing material into the surrounding environment and is modular in nature. Thus, a user may experience the benefits provided by the material being introduced into the surrounding environment and the wax warmer may be configured to aesthetically satisfy the user's desires as required. Also, the manufacturer of the wax warmer enjoys the benefits provided by producing an inexpensive yet easy to assemble device.

Numerous modifications to the present invention will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. A wax warmer, comprising:
a reservoir module for receiving a wax melt;
a heater module including a heating element and a first electrical connector to provide electrical power to the heating element, wherein the heater module further includes at least one inlet vent and at least one outlet vent; and
a base module including a sidewall having a flange that is between an upper and a lower end of the sidewall and extending from an interior surface of the sidewall, and a second electrical connector configured to releasably couple to the first electrical connector of the heating module to provide electrical power to the heating element,
wherein the heater module is retained on the flange, and
wherein the reservoir module, the heater module, and the base module are removable from one another in the normal use of the wax warmer and may be replaced by a second reservoir module, a second heater module, or a second base module, respectively.

2. The wax warmer of claim 1, wherein the heater module further includes a housing and the heating element is disposed within the housing.

3. The wax warmer of claim 2, wherein the heater module further includes a plate and the reservoir module is disposed on the plate, and wherein the reservoir module is in thermal communication with a first side of the plate and the heating element is in thermal communication with a second side of the plate.

4. The wax warmer of claim 3, wherein the base module includes an upper end and a lower end, and wherein the heater module is disposed on the upper end of the base module.

5. The wax warmer of claim 3, wherein the plate is a metal plate.

6. The wax warmer of claim 3, wherein the heater module includes at least one lug extending therefrom and the flange includes at least one gap adapted to receive the at least one lug of the heater module when the heater module is inserted into the base module.

7. The wax warmer of claim 6, wherein the heater module is retained on the base module by the at least one lug of the heater module being retained under the flange of the base module.

8. The wax warmer of claim 7, wherein at least one stop extends from the flange to restrain movement of the at least one lug of the heater module.

9. The wax warmer of claim 7, wherein the heater module is rotated in one of a clockwise or counterclockwise direction to retain the heater module on the base module.

10. The wax warmer of claim 7, wherein the heater module includes two lugs extending therefrom and the base module includes two flanges and two gaps adapted to receive the two lugs of the heater module when the heater module is inserted into the base module.

11. The wax warmer of claim 3, wherein the plate and an inner surface of the housing define a recess.

12. The wax warmer of claim 11, wherein a peripheral edge of the plate is spaced from the inner surface of the housing.

13. The wax warmer of claim 12, wherein the at least one outlet vent is provided between the peripheral edge of the plate and the inner surface of the housing.

14. The wax warmer of claim 13, wherein the plate rests on a plurality of spacer projections extending from the housing.

15. A wax warmer, comprising:
a reservoir module having a wax melt secured thereto;
a heater module including a heating element and a first electrical connector to provide electrical power to the heating element; and
a base module including a sidewall, a flange extending from an inner surface of the sidewall, and a second electrical connector configured to releasably couple to the first electrical connector of the heating module to provide electrical power to the heating element,
wherein the heater module is retained on an upper end of the sidewall and the flange of the base module and the reservoir module is releasably retained on an upper end of the heater module, and wherein a user may release the reservoir module from the heater module to replace the reservoir module in normal use of the wax warmer.

16. The wax warmer of claim 15, wherein the wax melt is irremovably attached to the reservoir module prior to melting of the wax melt.

17. The wax warmer of claim 16, wherein the wax melt is attached to the reservoir module by at least one of an adhesive, a chemical bond between the wax melt and a surface of the reservoir module, an interference fit between surfaces of the wax melt and surfaces of the reservoir module, and a projection extending from the reservoir module into the wax melt.

18. The wax warmer of claim 15, wherein the reservoir module, the heater module, and the base module are included in a kit, and wherein the kit further includes at least one wax melt.

19. The wax warmer of claim 1, wherein the second electrical connector is configured to releasably couple to the first electrical connector using a plug and a socket.

20. The wax warmer of claim 15, wherein the second electrical connector is configured to releasably couple to the first electrical connector using a plug and a socket.

21. A wax warmer, comprising:
a reservoir module;
a heater module including a heating element and a first electrical connector to provide electrical power to the heating element; and
a base module including a sidewall, a flange extending from an inner surface of the sidewall, and a second electrical connector configured to releasably couple to the first electrical connector of the heating module to provide electrical power to the heating element,
wherein the heater module is retained on an upper end of the sidewall and the flange of the base module and the reservoir module is releasably retained on an upper end of the heater module.

* * * * *